United States Patent [19]
Froehlich et al.

[11] Patent Number: 5,551,419
[45] Date of Patent: Sep. 3, 1996

[54] CONTROL FOR CPAP APPARATUS

[75] Inventors: James P. Froehlich, Berlin; Joseph N. Mitchell, Rockwood; Stephen M. Jones, Turtle Creek, all of Pa.

[73] Assignee: DeVilbiss Health Care, Inc., Somerset, Pa.

[21] Appl. No.: 356,471

[22] Filed: Dec. 15, 1994

[51] Int. Cl.⁶ ..................................... A61M 16/00
[52] U.S. Cl. ................ 128/204.23; 128/204.26; 128/205.25
[58] Field of Search ............... 128/204.18, 204.21, 128/204.23, 204.26, 205.13, 205.18, 205.24, 205.25

[56] References Cited

U.S. PATENT DOCUMENTS

| Re. 29,778 | 9/1978 | Stewart | 128/204.25 X |
|---|---|---|---|
| 4,239,039 | 12/1980 | Thompson | 128/205.24 |
| 5,065,756 | 11/1991 | Rapoport | 128/204.18 |
| 5,117,819 | 6/1992 | Servidio et al. | 128/204.18 |
| 5,134,995 | 8/1992 | Gruenke et al. | 128/204.23 |
| 5,148,802 | 9/1992 | Sanders et al. | 128/204.18 |
| 5,161,525 | 11/1992 | Kimm et al. | 128/204.26 |
| 5,199,424 | 4/1993 | Sullivan et al. | 128/204.18 |
| 5,203,343 | 4/1993 | Axe et al. | 128/725 |
| 5,239,995 | 8/1993 | Estes et al. | 128/204.23 |
| 5,245,995 | 9/1993 | Sullivan et al. | 128/204.23 |
| 5,259,373 | 11/1993 | Gruenke et al. | 128/204.23 |
| 5,313,937 | 5/1994 | Zdrojkowski | 128/202.22 |
| 5,335,654 | 8/1994 | Rapoport | 128/204.23 |
| 5,433,193 | 7/1995 | Sanders et al. | 128/204.18 |

FOREIGN PATENT DOCUMENTS

| 2112884 | 7/1994 | Canada . |
|---|---|---|
| 2694697 | 2/1994 | France . |
| 2695320 | 3/1994 | France . |
| WO89/05669 | 6/1989 | WIPO . |
| WO92/22244 | 12/1993 | WIPO . |
| WO93/25260 | 12/1993 | WIPO . |
| WO94/06499 | 3/1994 | WIPO . |
| WO94/13349 | 6/1994 | WIPO . |

OTHER PUBLICATIONS

Copy of brochure on the Puritan–Bennett Companion 318 Nasal CPAP System dated May, 1993.
Copy of brochure on "The Sullican Nasal VPAP System" dated Jun., 1994.

*Primary Examiner*—Stephen Funk
*Assistant Examiner*— Eric P. Raciti
*Attorney, Agent, or Firm*—MacMillan, Sobanski & Todd

[57] ABSTRACT

The invention relates to continuous positive airway pressure (CPAP) respiratory therapy apparatus for treatment of apnea, hypopnea and other sleep disorders, and particularly to a control for the CPAP apparatus. A blower is connected through a hose and a mask, such as a nasal mask or a nasal cannula, to the patient's respiratory airway. An air flow sensor and an air pressure sensor are located at the blower end of the hose. Optionally, a vent valve also may be located at the blower end of the hose. The sensor outputs are used to estimate the air pressure at the mask and the air flow sensor output is used to determine the gross air flow to the hose, the patient air flow and the occurrence of patient snoring. The air flow sensor output also is used to generate a square wave breathing signal. The breathing signal may be used by a microprocessor to control the optional vent valve to establish different levels in the applied pressure during inspiration and expiration. The applied CPAP pressure may be increased in response to the detection of apnea and hypopnea events. The microprocessor detects and ignores mask leaks, open mouth breathing and exhale puff breathing.

15 Claims, 7 Drawing Sheets

CONTROL FOR CPAP APPARATUS

TECHNICAL FIELD

The invention relates to respiratory therapy for treatment of sleep apnea, hypopnea, snoring and similar respiratory conditions and more particularly to an improved control for continuous positive airway pressure (CPAP) respiratory therapy apparatus.

BACKGROUND ART

Many sleep related respiratory conditions are caused by a blockage or a partial blockage of the respiratory tract. Snoring, for example, is caused by a partial blockage of the respiratory tract during inhalation. As the blockage increases, hypopnea or a reduction of air flow to the lungs occurs. Apnea, or a temporary cessation of breathing, can occur when the airway becomes totally blocked. A patient suffering from apnea may stop breathing for reoccurring intervals of from 10 seconds to two minutes or more for severe cases. The sleep apnea patient may have difficulty functioning in a normal manner during the day because of insufficient sleep caused by the apnea events. In severe cases, the patient also can suffer from problems caused by reduced blood oxygen levels.

One form of treatment for severe snoring, hypopnea, sleep apnea and certain other respiratory conditions involves the application of a pneumatic splint to the patients respiratory tract while the patient sleeps. A sufficiently high continuous positive pressure is applied to the patient's airway to prevent its collapse or blockage. Typically, the applied positive pressure is within the range of from 3 to 20 cm $H_2O$. When the CPAP apparatus is initially turned on, the apparatus may immediately apply the prescribed pressure to the patient's airway. However, for improved patient comfort which in turn encourages patient compliance with the physicians prescribed treatment, it is desirable to maintain the applied pressure as low as possible while providing the desired therapeutic treatment. Various techniques have been used to minimize the applied pressure. For example, a more comfortable low pressure may be applied to the patient while the patient falls asleep. Generally, the patient will not suffer from hypopnea or apnea during this time. After sufficient time has elapsed for the patient to fall asleep, a controller gradually increases the applied pressure to the prescribed therapeutic level. Such a control process is sometimes referred to as a "soft start". When the mask is first attached to the patient and the CPAP therapy apparatus is turned on, the pressure controller also may be manually or automatically cycled to apply the full prescribed pressure to the patient for a short time to allow the patient to check and adjust for mask leaks before going into a soft start cycle.

In another known type of CPAP respiratory therapy apparatus, the pressure is automatically increased in increments from an initial low pressure in response to the sensing of snoring, hypopnea and/or apnea events. The pressure also may be gradually decreased over a period of time in the absence of such events. Further, the CPAP therapy apparatus may delay any pressure increase for a time sufficient for the patient to fall asleep or may immediately look for abnormal breathing patterns. Systems of this type often sense snoring and other sounds occurring in the respiratory tract as precursors of apnea, or they may sense the absence of changes in the flow or pressure occurring between inhalation and exhalation during an apnea event, or they may sense the patient's breathing pattern through chest expansions and contractions.

The prior art systems which automatically adjust the pressure respond to specific conditions. Unfortunately, the sensors and the controllers are not capable of distinguishing between different conditions which have similar responses. For example, some systems assume that any cessation of breathing results from apnea and accordingly the pressure is incrementally increased up to the maximum prescribed pressure. If the mask is accidentally knocked off or removed by the patient during sleep or if the mask is moved to a position creating leakage between the mask and the patient's face or if the patient begins open mouth breathing, an automatic pressure controller may assume that the patient has stopped breathing because of an apnea event or slowed down breathing because of hypopnea and may automatically increase the pressure to the maximum prescribed level. Another condition which can result in an automatic pressure increase is exhale mouth puffs. Here the patient inhales through the nose and exhales through the mouth. The prior art controllers cannot detect this condition and consequently may consider the breathing to be shallow and increase the applied pressure. If a patient undergoing CPAP therapy must get up and temporarily remove the mask during the night, it is necessary for the patient to remember to manually restart the CPAP controller when the mask in reattached. If the apparatus is left on while the mask is temporarily removed, the controller will respond as if the patient has experienced an apnea event and will increase the mask pressure to the maximum level. The patient then will be subjected to the maximum pressure when the mask is reattached.

DISCLOSURE OF INVENTION

According to the invention, an improved control is provided for accurately detecting different types of patient breathing and for detecting gross mask leaks, and for making appropriate pressure adjustments. The controller operates in response to the patient breathing pattern. Patient breathing is sensed by sensing air flow to a mask connected to the patient's airway and an estimated air pressure at the mask. In the prior art, the mask pressure was measured by a secondary tube run from the mask along the patient tubing back to a pressure sensor at the main console which houses the blower and controller. According to one aspect of the invention, the pressure and flow rates are measured directly at a console from the pressure and air flow delivered to the air hose connected to the patient. The measured pressure and flow rates and pressure drop rs. flow properties for the patient air hose are used to accurately estimate the actual mask pressure. As used herein, the term "mask" and "nasal mask" are intended to include a nasal mask which seals over a patient's nose, a face mask which seals over the mouth and nose of a patient, a cannula which seals to the nares of a patient's nose, and any similar device which is capable of applying a positive airway pressure to the patient's respiratory system. The term "blower" shall mean any device capable of creating air flow at a positive pressure suitable for respiratory therapy.

From the measured pressure and flow signals, the control determines the actual mask pressure, the total flow of air to the mask, the actual flow of air to the patient's respiratory system and generates a breathing signal. The breathing signal is a square wave which changes logic levels at the beginning of inspiration and at the beginning of expiration. This information is supplied to a programmed microprocessor. The microprocessor also receives a speed signal from the blower. Switches are provided for entering a maximum prescribed CPAP pressure. The blower speed is controlled in response to the blower speed signal, the programmed CPAP level and the total flow signal and a calculated inspiratory positive airway pressure (IPAP) based on the patient's breathing patterns. If desired, the apparatus may be operated in a bilevel mode in which the applied pressure is reduced by opening a vent valve during expiration, or in which the blower is run at a pressure above the IPAP level and the patient pressure is reduced to the desired expiratory positive airway pressure (EPAP) level during expiration and to the desired IPAP level during inspiration by opening a vent valve to a more and less degree, respectively. The microprocessor is programmed with a desired EPAP level which is lower than the IPAP level.

The control is capable of detecting and accommodating excessive mask leaks and mouth breathing wherein the patient keeps his or her mouth open while breathing through the nose so that some of the delivered positive pressure air flow is continuously discharged or leaks through the mouth. These air leaks distort the flow signal significantly once a certain leak level is achieved. The automatic pressure adjust algorithm uses the flow signal's peak to peak values to identify when a respiratory event has occurred. If leaks are not detected, the algorithm will score the flow reduction as an event causing the pressure to be increased, eventually to a much higher CPAP level than is required to maintain airway patency. If a leak above a threshold level is detected, the algorithm ignores any events that are scored until the leak level drops below the threshold. This problem may be resolved simply by selecting a different size or style of mask for the patient or by applying a chin strap to keep the mouth closed.

The breathing signals also may be distorted by exhale puffing in which the patient inhales through the mask and opens his or her mouth while exhaling. The prior art systems also responded to exhale puffing by increasing the applied pressure. The algorithm identifies exhale puffing and does not score a respiratory event. Consequently, the pressure is not increased when exhale puffing is detected.

The CPAP apparatus of the invention may be used to provide the treating physician or therapist with greater information than was previously available by connecting the apparatus to a recorder. The recorder may indicate the total time the apparatus is used by the patient, normal breathing, snoring, hypopnea and apnea events, open mouth breathing or excessive mask leaks, and exhale mouth puffing.

Accordingly, it is an object of the invention to provide a controller for automatically operating an air blower in CPAP apparatus.

Other objects and advantages of the invention will become apparent from the following detailed description of the invention and the accompanying drawings.

BEST MODE FOR CARRYING OUT THE INVENTION

Figure 1:
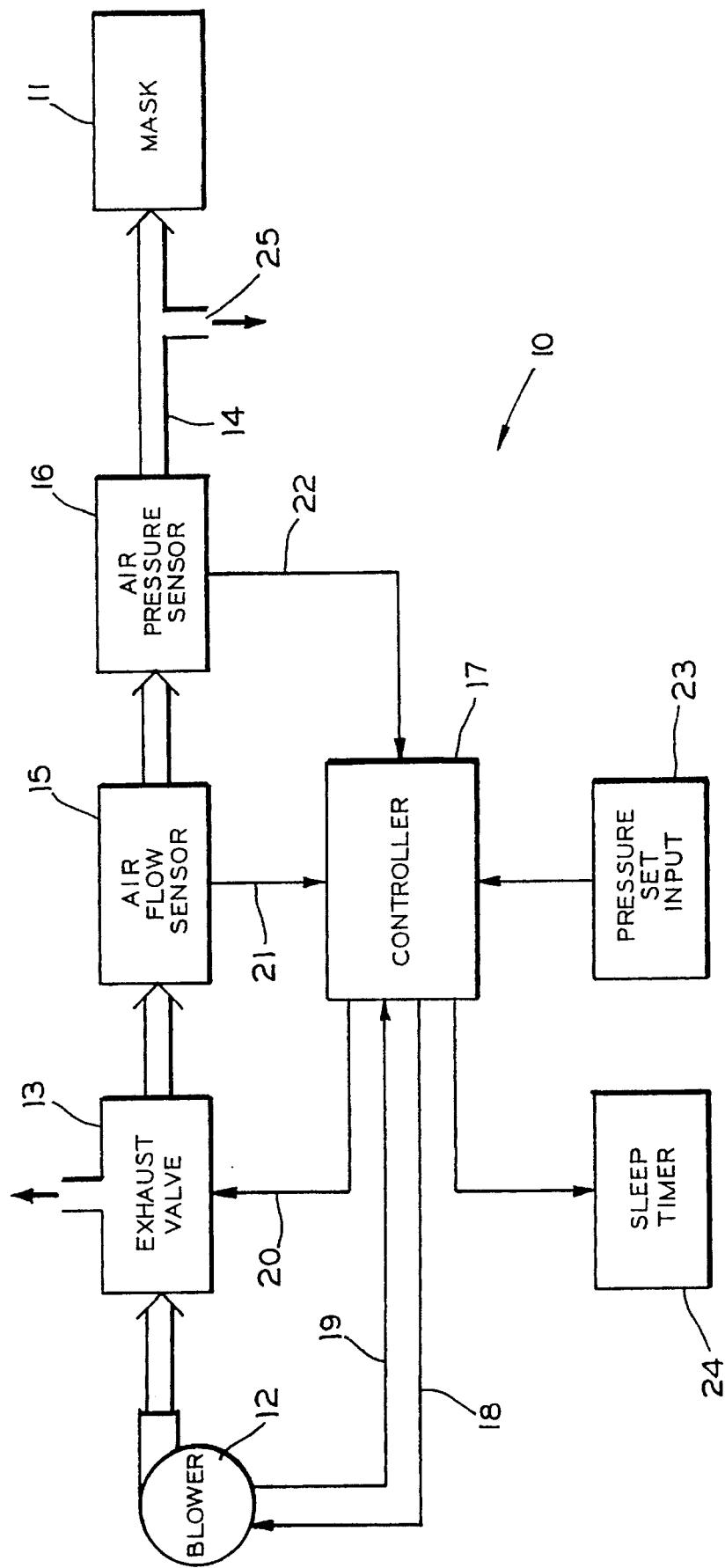
FIG. 1 is a block diagram of CPAP apparatus according to the invention.

Referring to FIG. 1 of the drawings, a block diagram is shown for CPAP apparatus 10 according to a preferred embodiment of the invention. The apparatus 10 has a mask 11 which is secured to a patient by suitable straps or headgear (not shown) in a conventional manner. The mask 11 may be, for example, a nasal mask which covers and is sealed to the patient's face around the nose, a face mask which covers and is sealed around both the nose and mouth or a nasal cannula which engages and seals to the patient's nares.

A centrifugal blower 12 or other suitable source of compressed air is connected through an optional exhaust valve 13 and a flexible, kink resistant pressurized air delivery tube 14 to the mask 11. A flow sensor 15 and a pressure sensor 16 are connected at any point downstream of the exhaust valve 13 to measure air flow and air pressure delivered through the mask 11 to a patient. The apparatus 10 is operated by a controller 17 which includes signal processing circuitry and a programmed digital microprocessor. The controller 17 is connected through a line 18 to drive the blower 12 and the blower 12 is connected through a line 19 to provide a speed feedback signal to the controller 17. The controller 17 is connected through a line 20 to control the optional exhaust valve 13, as will be discussed below. The air flow sensor 15 provides an accurate air flow rate signal over a line 21 to the controller 17 and the air pressure sensor 16 provides an air pressure signal over a line 22 to the controller 17.

The air flow rate sensor 15 must be capable of providing an accurate flow rate signal which responds to air flow variations between inspiration and expiration and ideally the sensor 15 also is sufficiently sensitive to be responsive to flow fluctuations caused by snoring. Preferably, the air flow sensor 15 consists of a laminar flow element (not shown) connected in series with the air delivery tube 14 and a mass flow transducer (not shown). The laminar flow element and the mass flow transducer are connected in parallel. Most of the air flow from the blower 12 to the tube 14 passes through the laminar flow element to create a pressure drop which is directly proportional to the air flow rate. A smaller portion of the air flow will pass through the mass flow transducer to produce a signal which is directly proportional to the pressure drop across the laminar flow element and hence a signal which is directly proportional to the total air flow delivered to the tube 14.

The prescribed maximum CPAP pressure, or the inspiratory positive airway pressure (IPAP) is set by a suitable input device 23, such as pressure set switches, which are connected to or a part of the controller 17. Finally, the controller 17 may be connected to an optional sleep timer 24 which measures the total time that the patient is wearing the mask 11. It will be appreciated that the blower 12, the exhaust valve 13, the sensors 15 and 16, the controller 7, the pressure set input 23 and the sleep timer 24 may all be mounted in a single base unit cabinet (not shown) connected through the hose 14 to the mask 11. Since the air pressure in the mask 11 is a function of the pressure inside the base unit and the pressure loss in the delivery hose 14, which in turn is a function of the flow through the hose 14, the pressure signal and the flow signal may be combined to produce a signal that accurately represents the pressure at the mask 11. The signals may be combined in the controller either with analog circuitry or digitally by the programmed microprocessor.

The controller 17 may operate the blower 12 to provide one or more of several known operating modes. When the apparatus 10 is turned on in one known type of CPAP apparatus, the blower 12 is operated to immediately provide the prescribed pressure through the mask 11 to the patient. In another known type of CPAP apparatus, the blower 12 initially applies a low pressure to the patient for improved patient comfort while falling asleep. Patient compliance with the prescribed therapy is increased by promoting patient comfort. According to one method, the pressure is gradually ramped up over a time selected either by the physician or by the patient. According to another method, after a set time delay sufficient for the patient to fall asleep, the apparatus automatically ramps the pressure up to the prescribed pressure. If desired, a switch may be provided for the patient to restart the time delay if he or she has not fallen asleep during the initial delay. These modes of operation are sometimes referred to as "soft start". Or, the apparatus may have an automatic operating mode which initially starts at a low pressure and automatically adjusts the applied pressure up and down, but no greater than a set maximum prescribed pressure. Adjustments may be based on sensing the presence and absence of hypopnea and/or apnea events and/or precursors to apnea such as snoring. Apparatus of this type tries to maintain the minimum pressure necessary to prevent the occurrence of hypopnea and apnea events. The automatic adjustments may begin immediately after the apparatus 10 is turned on or they may begin after a soft start time delay. The automatic systems may detect apnea and hypopnea by known techniques. Apnea is broadly defined as the cessation of breathing. An apnea event may be scored, for example, by detecting when the air flow to the patient drops below a predetermined level for a predetermined time. For example, if the patient air flow drops below a threshold level for 10 seconds, this may be considered an apnea event. Hypopnea is defined as a reduction in patient air flow. If, for example, the patient air flow drops to 40% of the average patient air flow for 0 seconds, this may be scored as a hypopnea event. Based on the frequency and nature of the detected respiratory events, the applied CPAP pressure may be incrementally increased or decreased to maintain the minimum needed pressure to prevent apnea and hypopnea events.

The controller 17 also may provide a standby operating mode for the blower 12. When the apparatus 10 is initially turned on, the blower 12 may remain off or it may be operated at a low speed to provide a constant low air flow to the mask 11. When the controller 17 senses breathing in the mask 11, the controller 17 begins either a soft start cycle or an auto adjust cycle which is responsive to the detection of hypopneas, apneas and/or precursors to apnea such as snoring. If the blower 12 is initially operated at a low pressure standby mode for a predetermined time, such as 15 minutes, without sensing breathing, the controller 17 may turn the blower 12 off.

Normally, one or more calibrated vent openings 25 are provided either in the mask 11 or in the delivery tube 14 adjacent the mask 11. A portion of the air flow through the tube 14 and expiratory air from the patient are discharged through the vent opening 25. When the patient inhales, the air pressure as sensed by the sensor 16 will drop slightly and when the patient exhales, the air pressure sensed by the sensor 16 will tend to increase slightly. The positive airway pressure provides a pneumatic splint to keep the airway expanded during inhalation for free air flow to the lungs. The level of the pneumatic splint generally is not needed during exhalation. A reduced pressure is sometimes needed during exhalation since the patient must exhale against any applied pressure. Exhaling against the IPAP pressure also can cause some patient discomfort. The optional exhaust valve 13 may be used to reduce the applied pressure during exhalation. When the controller 17 senses that expiration has began, the exhaust valve 13 may be opened to vent a portion of the air flow from the blower 12 to atmosphere, thus reducing the EPAP level at the mask 11. The exhaust valve 13 also may be used to control the IPAP level as well as the EPAP level. Thus the CPAP apparatus 10 may be operated in a bilevel mode wherein different pressures are applied to the patient during inhalation and exhalation. If the apparatus 10 is provided with a bilevel operating mode, both the desired EPAP pressure and the desired IPAP pressure may be set with the pressure set input 23.

Figure 2:
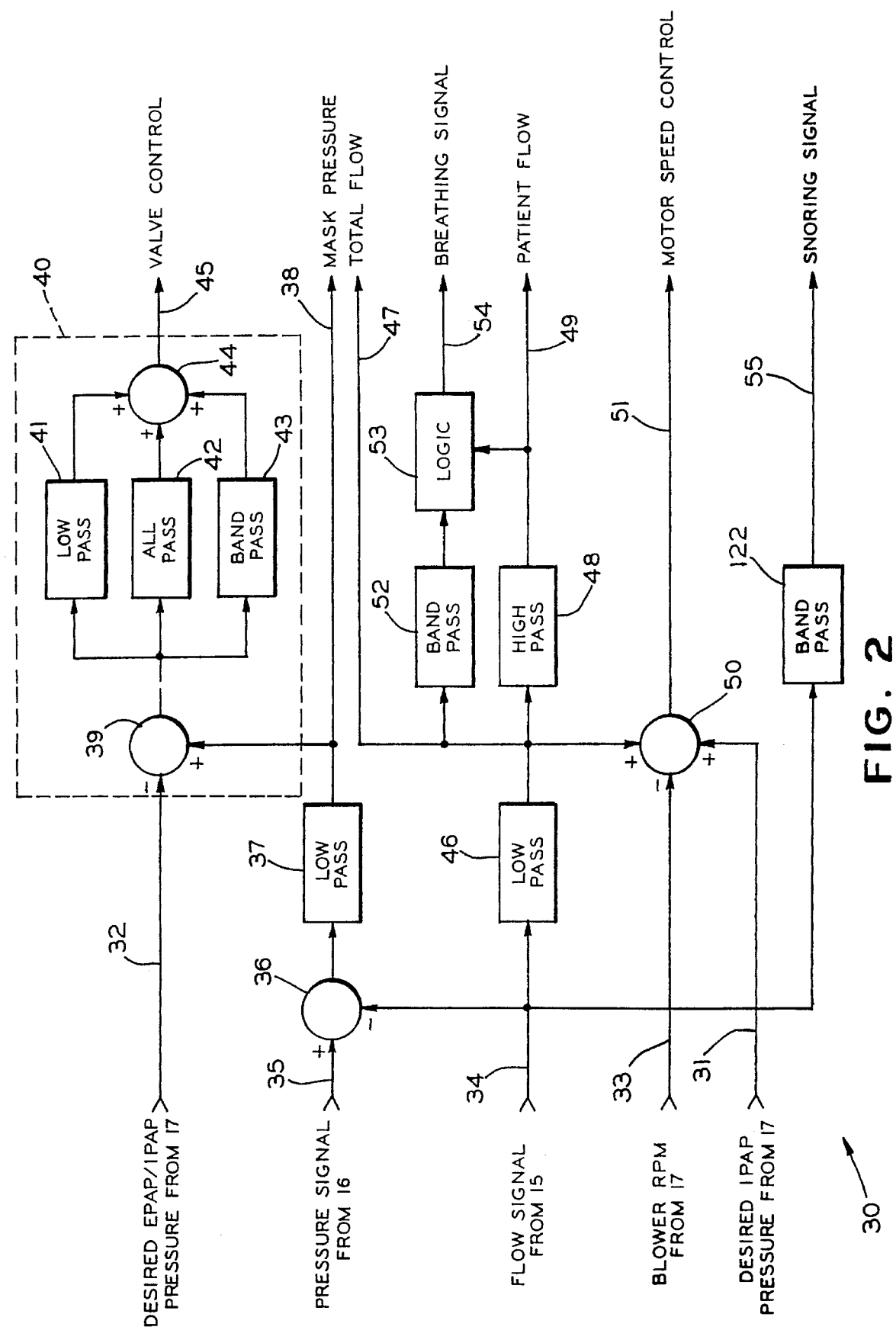
FIG. 2 is a schematic block diagram of signal filtering circuitry portion of the controller of FIG. 1.

FIG. 2 is a block diagram of a portion of the controller 17 illustrating circuitry 30 used in conjunction with a programmed microprocessor for controlling the blower 12 and the exhaust valve 13 and for providing information on the operation of the CPAP apparatus 10 according to one embodiment of the invention. The exemplary circuitry 30 has five analog inputs: an input 31 indicative of the desired IPAP pressure, an input 32 from the microprocessor indicative of the desired EPAP or IPAP pressure, an input 33 representing the actual blower speed from the line 18 (FIG. 1), an input 34 representing the air flow in the hose 14 from the sensor 15 (FIG. 1) and an input 35 representing the air pressure delivered to the hose 14 from the sensor 16 (FIG. 1). The desired IPAP pressure input 31 and the desired EPAP input 32 are analog signals which may be established by the microprocessor and the pressure set inputs 23. If the apparatus 10 does not have a bilevel operating mode, then the EPAP input 32, the filter 40, the valve control output 45 and the exhaust valve 13 are omitted. The input 31 then becomes redefined as indicative of the desired CPAP pressure.

As indicated above, the estimated pressure at the mask 11 is a function of the pressure signal and the flow signal as measured by the sensors 16 and 15, respectively, and the pressure drop along the hose 14. The pressure signal on the input 35 and the flow signal on the input 34 are combined at an amplifier 36 to produce a signal representing the mask pressure. It will be appreciated that the mask air pressure will be equal to the air pressure at the blower end of the hose 14 less the pressure drop along the length of the hose, which is a function of the air flow through the hose and the flow resistance of the hose. The greater the air flow through the hose, the greater the pressure drop across the length of the hose. Both the air pressure and the air flow at the blower end of the hose 14 will vary with the patient's inspiration and expiration into the mask. The algorithm used to combine the pressure and flow signals must be determined based on the length and flow resistance of a particular hose 14 connected to the mask 11. This algorithm may be a simple correction factor determined by the gain of the flow signal input to the amplifier 36, or it may be a more detailed algorithm implemented, for example, by the microprocessor in place of the amplifier 36. The degree of accuracy of the estimated mask air pressure output will depend on the sophistication and accuracy of the algorithm used in combining the pressure and flow signals. The algorithm is most easily determined based on actual measurements of pressure drops across the hose 14 for a number of different flow rates. If the signals are combined in a microprocessor, a look-up table may be created from the measurements. The pressure drop across the hose can be looked up in the table for the air pressure at the blower end of the hose and this pressure drop is subtracted from the pressure to accurately estimate the mask pressure. The resulting estimated mask pressure signal is passed through a low pass filter 37 which attenuates high frequency noise and produces a clean mask pressure signal on an output 38.

The mask pressure signal on the output 38 and the desired EPAP or IPAP pressure signal on the input 32 are combined at an amplifier 39 in a filter 40 to create an error signal. In the filter 40, the error signal is applied through a low pass filter 41, an all pass filter 42 and a band pass filter 43, all connected in parallel, to a summing amplifier 44 to produce a valve control signal on an output 45 for operating the exhaust valve 13 (FIG. 1). The valve control signal is made up of a component which is proportional to the error signal, a component which is the integral of the error signal and a component which is the derivative of the error signal. The valve control output 45 controls how much air is vented by the valve 13 during both inhalation and exhalation. The microprocessor determines when exhalation is taking place and the valve 13 should be opened and controls the input 32 accordingly.

The flow signal on the input 34 also is passed through a low pass filter 46 which attenuates high frequency noise and produces a clean total air flow signal on an output 47. The low pass filter 46 removes snoring noise from the flow signal. The low pass filter 46 may have, for example, a cutoff frequency of about 20 Hz. The total air flow signal from the filter 46 also is applied through a high pass filter 48 which eliminates the DC component of the signal which is caused by continuous leakage flow through the expiration vent opening 25 and through any leakage between the mask and the patient's face. The DC flow signal component also may be caused in part by open mouth breathing when the patient keeps his or her mouth open while breathing through the nose. A portion of the air flow to the patient's nose may be continuously vented through the open mouth. The resulting output from the filter 48 is a patient flow signal which is applied to an output 49. This signal accurately represents the air flow to the patient's lungs during inspiration and from the patient's lungs during expiration.

The desired IPAP pressure motor control voltage is calculated at a summing amplifier 50 in response to the total flow signal from the low pass filter 46, the blower speed input 33 and the desired IPAP input 31 from the microprocessor to produce a motor speed control output 51 for establishing the desired inspiratory pressure at 100 LPM (liters per minute) total flow produced by the blower 12. The blower motor control voltage is constant for the desired IPAP. Below a pressure set point of 10 cm $H_2O$, the blower motor speed may be maintained at the 10 cm $H_2O$ set point, if desired.

For diagnostic purposes, it is sometimes desirable for the physician or the sleep clinician to have a record of the patient's snoring since it is an indication of a potentially unstable airway and is viewed by many as symptomatic of obstructive sleep apnea and as precursory to obstructive events. The propagation of sound in air is generally thought of as the localized alternating compression and rarefaction of the air and is usually detected as such. Consequent to the localized pressure cycling within the air is of course localized mass flow cycling. The localized mass flow cycling from snoring is carried from the mask 11 (FIG. 1) through the tube 14 to the mass air flow sensor 15. The sensor 15 is sufficiently sensitive to transduce the minute localized air flow variations caused by sound into electrical signals which then become superimposed onto the gross air flow signal. As is discussed in greater detail below, a snoring signal may be established and supplied to the microprocessor for recording by connecting the raw flow signal input 34 through a band pass filter and threshold comparator 122 to a snoring signal output 55.

Breathing Square Wave Generation And Bilevel Pressure Control

For producing a breathing signal square wave, the total flow signal from the low pass filter 46 also is passed through a band pass filter 52 which produces the mathematical derivative of the flow signal. The band pass filter 52 is of a type known as a "practical differentiator". The flow derivative signal is passed with the patient air flow signal from the high pass filter 48 to logic 53 which produces a square wave breathing signal output 54. The reason for using the total flow derivative in addition to the patient flow signal in generating the breathing square wave is that in certain circumstances the derivative of the total flow signal responds more quickly to inspiratory and expiratory efforts than the patient flow signal. The breathing square wave is used, for example, by the microprocessor for determining when to change operating modes and for controlling the opening and closing of the optional exhaust valve 13 (FIG. 1).

Ideally, the patient air flow signal would be a smooth, noiseless signal. Theoretically, detection of the initiation of inspiratory and expiratory efforts would involve feeding the patient flow signal and a DC reference signal representing zero patient flow into a comparator. The output of the comparator would then indicate which phase of breathing the patient was in and when phase transitions occur. The transition of the comparator output from a low to a high indicates the occurrence of an inspiratory effort. The transition of the comparator output from a high to a low indicates the occurrence of an expiratory effort. The problem is, however, that there is always some electrical noise on the patient flow signal as well as on the DC reference signal. At the end of an inspiratory phase or at the end of an expiratory phase, if the patient flow signal hovers near the DC reference signal for any length of time, noise present in both signals can cause the signals to crisscross over each other in a somewhat random manner, causing the output of the comparator to randomly toggle high and low when in fact no breathing phase transition has yet occurred. In order to avoid false signals, inhalation and exhalation signals and their derivatives are compared to reference limits above and below the DC reference signal. The reference limits are varied as a function of time and as a function of the peaks and valleys of the patient air flow signal and of the derivative of the total air flow signal to maintain the sensitivity of the breathing signal over a wide range of patient breathing patterns.

Figure 3:
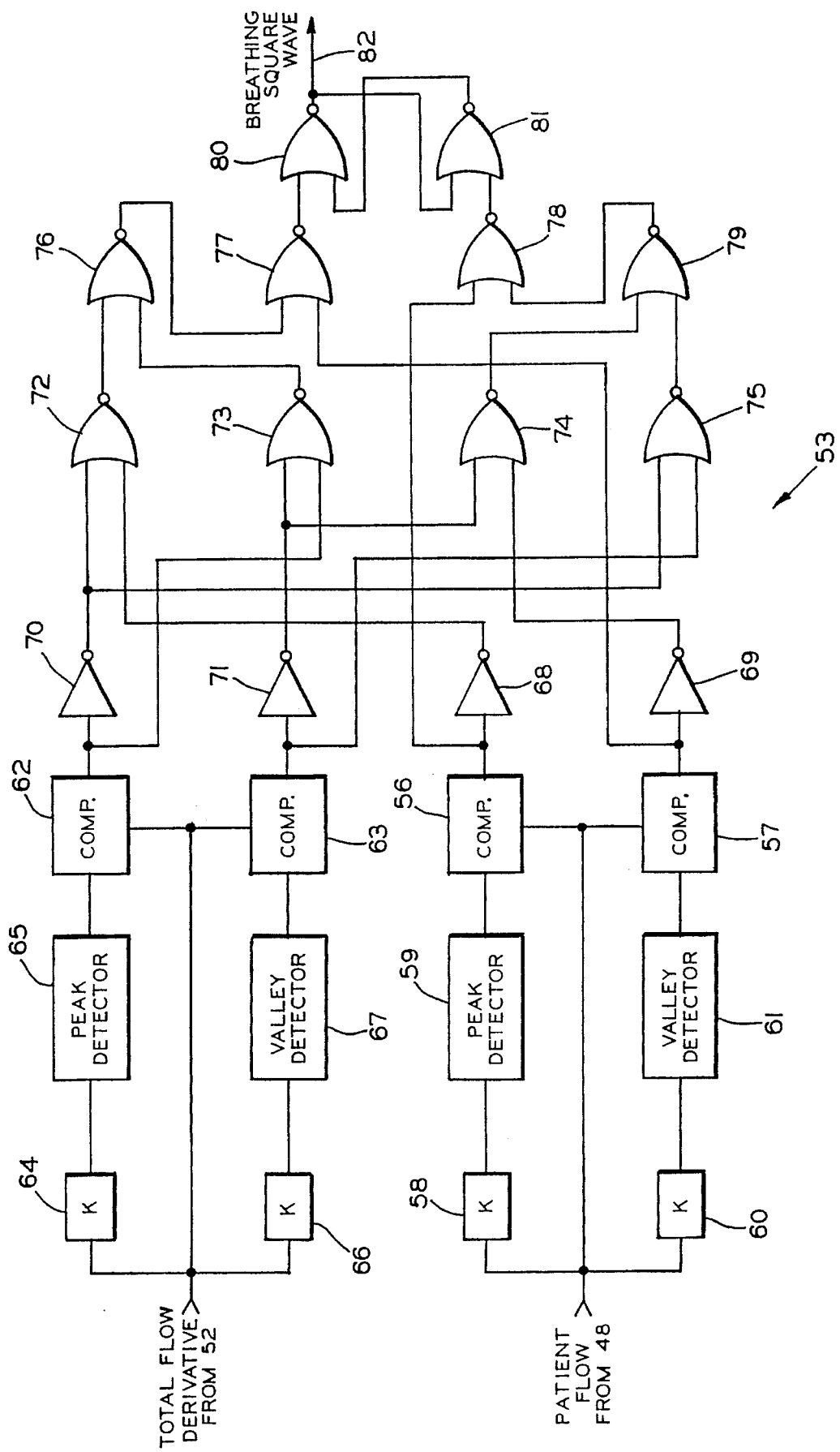
FIG. 3 is a schematic block diagram showing details of the logic for detecting the beginning of patient inspiration and expiration.

FIG. 3 is a schematic diagram of the logic 53 for creating a square wave breathing signal. The patient air flow signal from the high pass filter 48 (FIG. 2) is applied to one input of a peak comparator 56 and to one input of a valley comparator 57 for comparison with threshold levels. The patient air flow signal also is passed through an amplifier 58, which reduces the signal level by a desired factor K to obtain the peak threshold limit on the signal peaks during inhalation, and onto a peak detector 59. The peak detector 59 produces a threshold limit output voltage having a maximum level of the peaks of the patient flow signal during inspiration and has a slow controlled decay from the peaks. If the patient's breathing level decreases, the maximum peak level will decrease to gradually decrease the threshold limit, while the threshold limit will immediately increase as the level of the breathing peaks increases. The comparator 56 generates a high output whenever the level of the patient flow signal exceeds the level of the output from the peak detector 59 to indicate that inspiration is taking place, and a low output otherwise. Similarly, the patient flow signal passes through an amplifier 60 to a valley detector 61 which produces a low level threshold limit voltage. The valley detector 61 is merely a peak detector which looks at the negative peaks of the patient flow signal and has the same slow controlled decay as the peak detector 59. The comparator 57 compares the inverse of the patient flow signal with the output of the valley detector 61 and produces a high output level whenever the patient flow signal is lower than the threshold level signal from the valley detector 61 to indicate that expiration is taking place, and a low output otherwise.

Figure 4:
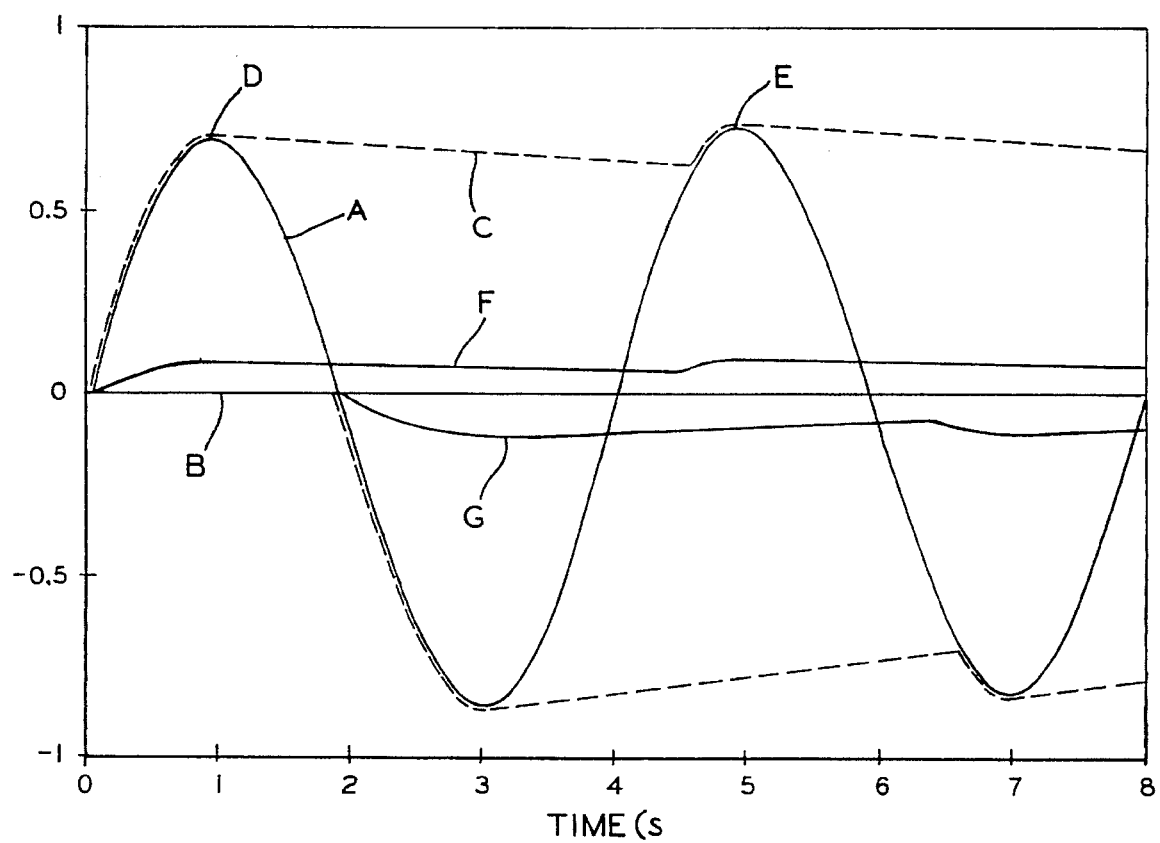
FIG. 4 is an exemplary and idealized patient air flow signal.

FIG. 4 is an exemplary patient flow signal A idealized as a simple sine wave whose frequency is 0.25 Hz or 15 breaths per minute and illustrating the self adjusting reference limits. The flow signal A is above a zero reference B during inspiration and is below the reference B during expiration. The dashed line C represents the output of the peak detector 65 if the signal level is not reduced by the amplifier 64. It will be seen that the line C increased with the first positive rise of the signal A to a first peak D and slowly decays until it encounters the second rising peak E. It then follows the rising peak E to the maximum level and begins decaying until it reaches the next peak (not shown). However, the amplifier 64 reduces the level of the output of the peak detector 65 to produce the inspiration threshold level F. Whenever the comparator 62 senses that the level of the flow signal A exceeds the reference level F, it generates a high output. A similar process takes place with the negative portions of the flow signal A to produce at the output of the valley detector 61 a threshold level G. Whenever the comparator 57 senses that the flow signal A is less than the exhalation reference level G, it generates a high output.

The total air flow derivative from the band pass filter 52 (FIG. 2) is processed in an identical manner to the patient air flow signal. Referring again to FIG. 3, the total air flow derivative is applied to one input to a peak comparator 62 and to one input to a valley comparator 63. The derivative signal also is applied through an amplifier 64 to a peak detector 65 and through an amplifier 66 to a valley detector 67. The comparator 62 generates a low output whenever the total flow derivative exceeds a threshold level from the peak detector 65 and a high output otherwise, and the comparator 63 generates a low output whenever the total flow derivative is lower than a threshold level from the valley detector 67 and a high output otherwise.

The outputs from the four comparators 56, 57, 62 and 63 are applied, respectively, to the inputs of four inverters 68–71. The outputs from the comparators 56, 57, 62 and 63 and from the inverters 68–71 are combined by 8 NOR gates 72–79. The gate 72 has an input connected to the output from the inverter 68 and an input connected to the output of the inverter 70. The gate 73 has an input connected from the output of the comparator 62 and an input connected to the output of the inverter 71. The gate 74 has an input connected to the output of the inverter 69 and an input connected to the output of the inverter 71. The gate 75 has an input connected to the output of the inverter 70 and an input connected to the output of the comparator 63. The gate 76 has an input connected to the output of the gate 72 and an input connected to the output of the gate 73. The gate 77 has an input connected to the output of the gate 77 and an input connected to the output of the comparator 57. The gate 78 has an input connected to the output of the comparator 56 and an input connected to the output of the gate 79. Finally, the gate 79 has an input connected to the output of the gate 74 and an input connected to the output of the gate 75. A pair of NOR gates 80 and 81 are connected to form an RS latch. The output of the gate 81 is connected to one input to the gate 80 and the output of the gate 80 is connected to one input of the gate 81. An output 82 of the gate 77 is connected to the other input to the gate 80 and the output from the gate 78 is connected to the other input to the gate 81. The output 82 of the gate 80 is a square wave which goes high when inspiration begins and remains high until expiration begins, at which time it goes low. The square wave signal will remain at a given level until there is a change between inspiration and expiration.

Inspiration is defined by the logic 53 as either the total flow derivative being above an upper threshold limit and the patient flow signal being between upper and lower threshold limits, or the patient flow signal being above an upper threshold limit. Expiration is defined by the logic 53 as either the total flow derivative being below a lower threshold limit and the patient flow signal being between upper and lower threshold limits, or the patient flow signal being below a lower threshold limit. The slowly discharging peak and valley detectors adjust the switching limits to be appropriate to the instantaneous respiratory patterns. Small time delays may be added to the patient flow and total flow derivative switching signals in order to eliminate false triggering at low tidal volumes and breathing frequencies. If both the patient flow signal and the total flow derivative are within their respective limits, the breathing square wave remains at whatever value it achieved prior to the occurrence of this condition. Thus, once the square wave goes to a level indicating inspiration, it will remain at this level until expiration is detected and once expiration is detected, the square wave will go to and remain at the logic level indicating expiration until inspiration is again detected.

Bilevel pressure control to the patient is produced by using the breathing signal to control the control valve 13. Referring again to FIG. 2, the microprocessor applies a signal representing the desired IPAP pressure to the input 32 during inspiration and applies a signal representing the desired EPAP pressure to the input 32 during expiration. Since the blower was set to provide the IPAP pressure, the valve 13 will be closed during inspiration. The vent valve 13 is a linear valve which is opened by an amount necessary to reduce the pressure of the blower output to the set EPAP pressure during expiration. According to one embodiment of the invention, the valve 13 will be open to more and less degree during expiration and inspiration, respectively.

Standby and Startup Control Modes

The controller 17 may operate the CPAP apparatus in any of three modes: a low pressure standby mode with the blower 12 operating at a low speed, a normal operating mode, and a standby mode with the blower 12 turned off. When the apparatus 10 is initially turned on, it enters the low pressure standby mode. While the apparatus is in either of the two standby modes, it monitors for breathing into the mask 11. If no mask breathing occurs within a predetermined time, such as 15 minutes, after the apparatus 10 enters the low pressure standby mode, the controller 17 turns the blower off to 35 conserve energy, while continuing to monitor for mask breathing. When the patient begins breathing into the mask 11, the controller 17 senses the breathing and turns the blower 12 on if it was off and the controller 17 enters the normal operating mode. If the mask is removed from the patient or a gross leak occurs, for example, between the mask 11 and the patient's face, the controller 17 senses the unimpeded air flow and, after a short time, again places the blower 12 in one of the standby modes, such as the low pressure standby mode. After remaining in the low pressure standby mode for the predetermined time, the blower is switched off. Consequently, if a patient awakes during the night and temporarily removes the mask, the blower 12 reverts to the low pressure standby mode until the patient replaces and begins breathing into the mask. If the mask is not replaced within the predetermined time, the blower is stopped. If desired, an alarm may be sounded to alert the patient that the CPAP apparatus 10 has been placed in the standby mode, since the blower 12 also will automatically enter the standby mode if the mask is knocked off or removed while the patient continues to sleep. There have been observed instances of patients removing CPAP masks while sleeping.

As described above, the patient air flow signal and the total air flow signals may be used to produce a square wave signal which changes from a low level to a high level when the patient begins to inhale and changes from the high level to the low level when the patient begins to exhale. The leading edges of the signal level changes in the square wave breathing signal indicate the beginning of inhalation and the beginning of exhalation. The programmable microprocessor in the controller 17 can respond to the leading edges of the breathing signal to determine when breathing into the mask 11 has began for switching the blower from the standby mode to the normal operating mode. The microprocessor also can determine from the total flow signal and/or from the breathing signal when the mask has been removed and switch the blower back to the standby mode.

Figure 5:
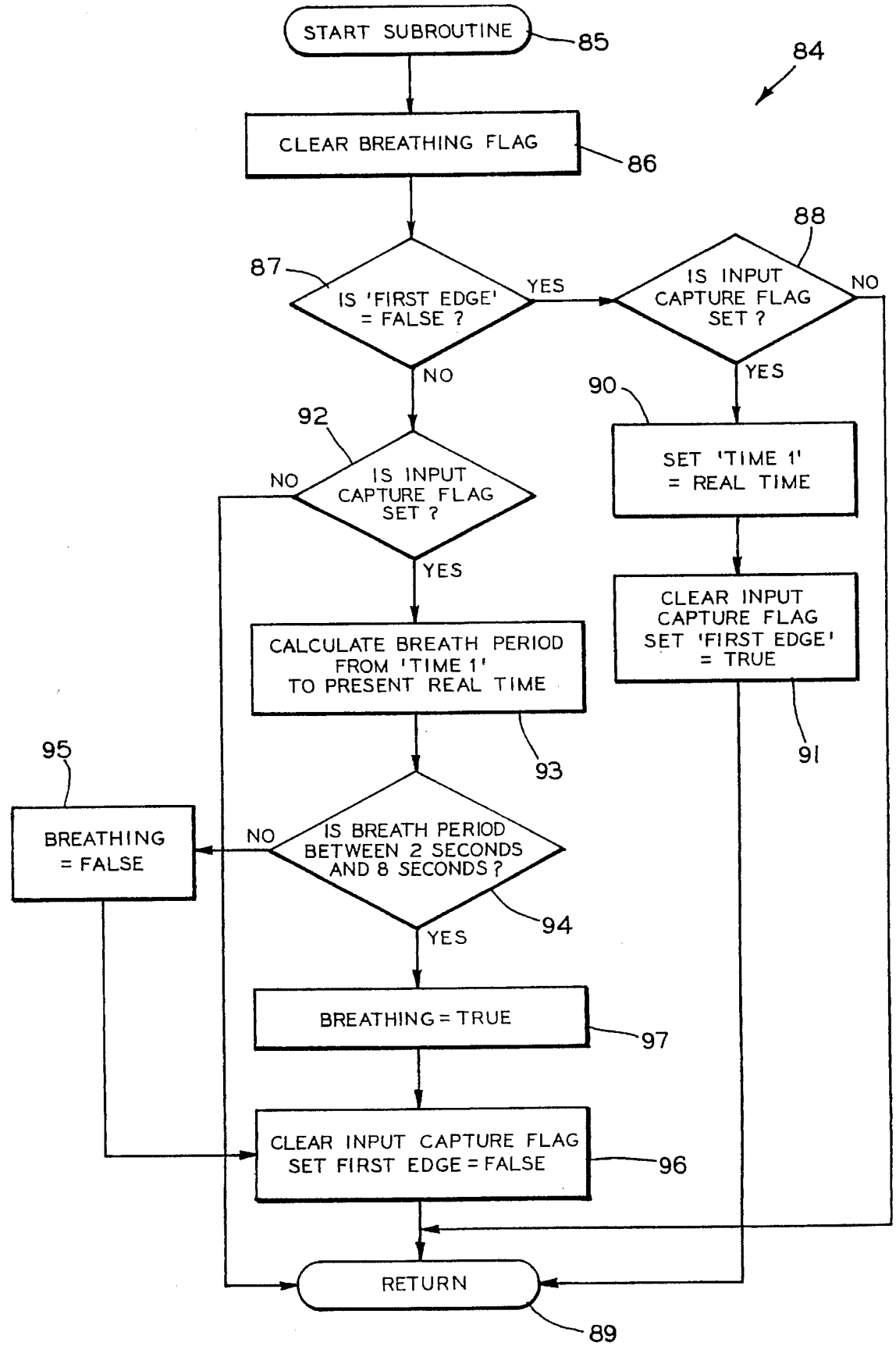
FIG. 5 is a logic flow diagram illustrating the automatic startup operation of the CPAP apparatus of FIG. 1 for switching from the standby mode to the normal operating mode.

FIG. 5 is a logic flow diagram illustrating a subroutine 84 for the microprocessor to determine when patient breathing into the mask 11 has began. An "input capture" flag is set each time the breathing square wave changes to a positive level at the beginning of an inspiration and remains set until cleared by the microprocessor. The subroutine 84 also uses a first edge flag and a breathing flag. The breathing flag is set true when breathing is detected and this flag tells the microprocessor to switch from the standby mode to the normal operating mode. The microprocessor cycles through the breathing subroutine on a periodic basis, for example, at a rate of 16 Hz., while the CPAP apparatus is in the standby mode.

The subroutine 84 is entered at a block 85 and passes through a block 86 wherein the breathing flag is cleared to a block 87. An inquiry is made at the block 87 as to whether the first edge flag is false. Prior to the first patient breath, the first edge flag is false and a block 88 asks if the capture flag is set. If the patient has not yet begun breathing into the mask 11, the capture flag will not be set and the logic passes through a return block 89 to the main program in the microprocessor. This cycle will repeat at a rate of 16 times per second until the breathing square wave changes to a logic level indicating the beginning of inspiration. At that time, the input capture flag is set and, during the next cycle through the subroutine 84, the block 88 causes a block 90 to store the present time as "time 1" in the microprocessor. The input capture flag then is cleared and the first edge flag is set to true at a block 91 and the subroutine passes through the return block 89 to the main program.

Since the first edge flag is now true, in the next cycle the control will pass from the block 87 to a block 92 which asks if the capture flag is set. The capture flag will not be reset until the patient begins a second breath into the mask. Until that time, the subroutine 84 passes from the block 92 to the return block 89. When the subroutine 84 is cycled immediately after the patient begins a second breath into the mask 11, the software passes from the block 92 to a block 93 which compares the stored time 1 with the present time to determine the breath period. A block 94 then looks at the breath period to determine if it falls within a normal breathing range. Normally, a person will breath at a rate of between 8 and 25 breaths per minute (BPM). For a preferred embodiment of the apparatus 10, it was decided to limit the breath period to between 2 seconds (30 BPM) and 8 seconds (7.5 BPM). If the breath period is outside of this range, the breathing flag is set to false at a block 95. Then the input capture flag is cleared and the first edge flag is set to false at a block 96 and the subroutine 84 is ended at the return block 89. On the other hand, if at the block 94 the breath period was found to be between 2 seconds and 8 seconds, the breathing flag is set true at a block 97. The cycle then passes through the block 96 to clear the input capture flag and set the first edge flag false and onto the return block 89. Once the breathing flag is set to true, the microprocessor switches from the standby mode to the normal operating mode and no longer cycles through the subroutine 84 until the apparatus 10 is returned to the standby mode.

Figure 6:
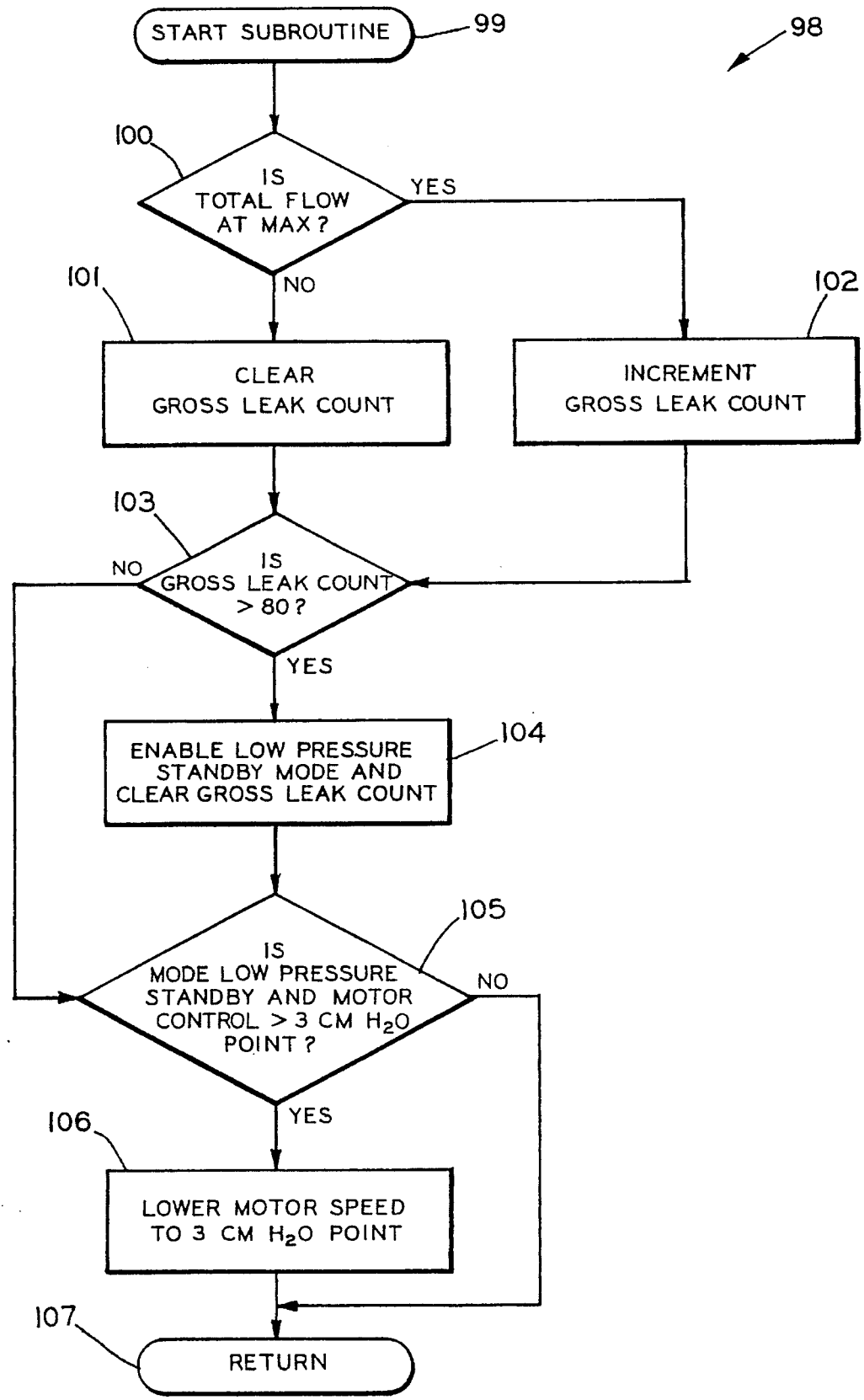
FIG. 6 is logic flow diagram illustrating the operation of the microprocessor for detecting gross air leaks in the CPAP apparatus of FIG. 1 for switching to the standby operating mode.

FIG. 6 is a logic flow diagram illustrating a subroutine 98 for causing the microprocessor to switch from a normal operating mode to a low pressure standby mode in the event of a gross air leak, for example, if the patient removes the mask 11 or if the mask 11 is moved to a position wherein the mask 11 fails to seal sufficiently against the patient's face. Each time the microprocessor cycles through its program at its 16 Hz. cycle time and the apparatus 10 is in the normal operating mode, the subroutine 98 is run. The subroutine 98 is entered at a block 99 and passes to a block 100 which asks if the total air flow is at a maximum, i.e., there is very little or no air flow resistance at the mask. For example, if the maximum blower output is 100 LPM (liters per minute), the total air flow may be considered to be at a maximum if it exceeds 75 LPM, since this level will not be exceeded unless there is a gross leak in the air flow system. If the total flow is not at the maximum, a gross leak counter is cleared at a block 101 and, if the total flow is at a maximum, the gross leak counter is incremented by 1 at a block 102. In either event, a block 103 then compares the gross leak count with the number 80. At the 16 Hz. cycle rate, it will take a continuous maximum air flow for 5 seconds to increment the gross leak count to 80. If the air flow drops below the maximum at any time during the 5 seconds, the gross leak count is cleared at the block 101. If the gross leak count exceeds 80, the low pressure standby mode is enabled and the gross leak count is cleared at a block 104. During the standby mode, the blower pressure is set to equal or below 3 cm $H_2O$. If the gross leak count at the block 103 was not greater than 80 or if the low pressure standby mode was set at the block 104, a block 105 asks if the apparatus 10 is set to the low pressure standby mode and also if the blower motor is operated to produce a pressure greater than the 3 cm H$_2$O point. If both questions are affirmative, the blower motor speed is reduced at a block 106 to the 3 cm H$_2$O pressure point and the subroutine returns at a block 107 to the main program. If either the apparatus 10 is not in the low pressure standby mode or the pressure is not greater than 3 cm H$_2$O at the block 105, the subroutine goes directly to the return block 107 without changing the blower motor speed. The apparatus 10 will remain in the low pressure standby mode either until mask breathing is detected and the normal operating mode is restarted or until the elapse of a predetermined time, such as 15 minutes, and the blower off standby mode is entered.

Since the blower is operated in the normal mode only while a patient breaths into the mask and there are no gross mask leaks, the blower operating time as measured by the timer 24 (FIG. 1) is an accurate indication of the time that the patient uses the apparatus 10. This information is often useful to the patient's physician or respiratory clinician.

Mask Leakage And Mouth Breathing Response

The apparatus 10 may be operated according to any of the known methods for detecting sleep apnea or precursors to sleep apnea. As is well known in the art, the pressure applied to the patient can be incrementally increased when apnea or a precursor to apnea is sensed. The applied pressure also may be decreased over a period of time when no events are detected. During sleep, patient movement may move the mask to a position wherein leaks occur between the mask and the patient's face. Although the leaks are present, they may not be so gross as to inhibit the effectiveness of the CPAP treatment. As discussed above, another source of air leakage may be open mouth breathing by the patient. When the CPAP pressure is applied to a patient's nose, most patients will keep their mouth closed while breathing through the nose. However, some patients may open their mouth while continuing to breath through the nose. Consequently, some of the applied air flow will be continuously vented through the open mouth and appear as an air leak. The tendency for open mouth breathing is reduced when the apparatus 10 is operated in a bilevel mode with reduced pressure during expiration. Still another type of mouth breathing is exhale puffing. Exhale puffing occurs when a patient inhales with the mouth closed, so that all inspiratory flow is provided by the CPAP apparatus, but opens the mouth to some degree while exhaling, with little or no expiratory flow driven back to the CPAP apparatus. The resulting breathing pattern is normal during inspiration and shallow or non existent during expiration. According to another aspect of the invention, mask leaks of a magnitude less than gross leaks but sufficient to otherwise appear as a respiratory event and mouth breathing are detected and ignored. The applied CPAP pressure is maintained constant after detecting any of these events.

In prior art automatic adjusting CPAP apparatus, mask leakage and mouth breathing were often scored as an apnea event, causing the pressure to be increased. Mouth breathing does not decrease with increasing pressure and in the case of open mouth breathing, higher pressures force the mouth open wider, creating a larger mouth leak. On the other hand, if mask leakage and open mouth breathing are treated as a gross leaks, the CPAP apparatus 10 would respond by entering the low pressure standby operating mode as discussed above. According to one aspect of the invention, the apparatus 10 detects and ignores lower level mask leaks and mouth breathing.

The microprocessor in the controller 17 averages the total flow signal over, for example, ten second intervals. This signal is compared with a predetermined flow rate which is used to indicate open mouth breathing and/or mask leakage. For example, if the maximum flow output from the blower 12 is 100 LPM, flow rates above 75 LPM may be used to indicate a gross mask leak at which the apparatus 10 is placed in the low pressure standby mode, as discussed above. Flow rates greater than 65 LPM and less than 75 LPM may be assumed to be caused by mask leakage and/or open mouth breathing. When a flow rate within this range is detected, open mouth breathing may be indicated on a recorder and the respiratory event detection variables are reset to prevent false apnea or hypopnea scores.

Figure 7:
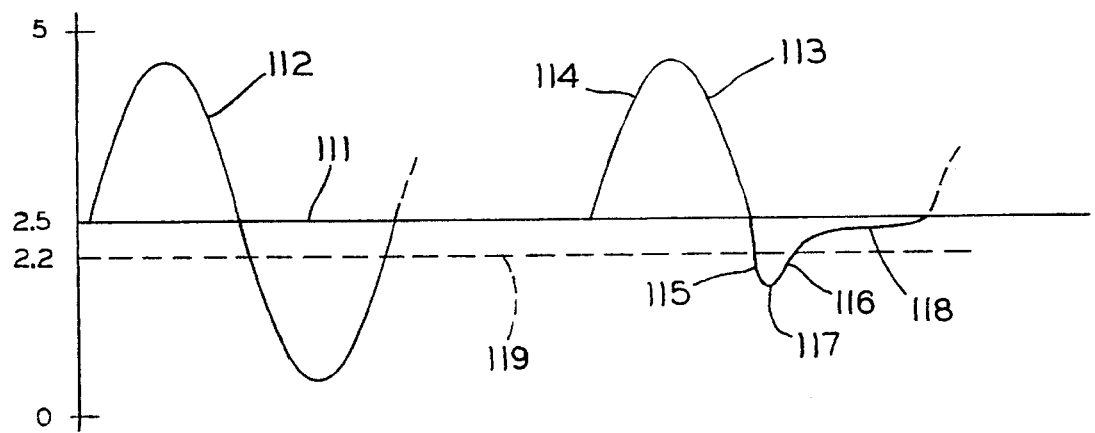
FIG. 7 is a graph comparing air pressure for an exemplary normal breath cycle with an exemplary exhale mouth puffing breath cycle.

Exhale mouth puffing is detected by monitoring the patient flow signal to determine the flatness of the expiratory phase of the breath cycle. The breathing square wave is used to determine the flatness of the expiratory phase of the breath cycle. FIG. 7 is a graph showing curves 112 and 113, respectively, of air flow through the tube 14 for an exemplary normal breath cycle on the left and for an exemplary exhale mouth puffing cycle on the right. The air flow signal is illustrated as being conditioned to vary from 0 volts to a maximum of 5 volts. In the illustrated graph, a zero flow rate to the patient produces a sensor voltage of 2.5 volts, as represented by the line 111. A sensor voltage below 2.5 volts indicates that the patient is exhaling and a sensor voltage above indicates that the patient is inhaling. Thus, the line 111 represents the dividing crossover between inspiration and expiration. The sensor voltage is illustrated as increasing to about 4.5 volts during at the peak inspiration flow and dropping to about 0.5 volts at the peak expiration flow for the exemplary normal breath cycle curve 112. During exhale mouth puff breathing, an inspiration portion 114 of the curve 113 is the same as the inspiration portion of the curve 112 for the normal breath cycle. An initial portion 115 of an expiration portion 116 of the curve 113 begins as a normal curve. However, at a point 117 the patient opens his or her mouth and begins to exhale through the mouth. As a consequence of the open mouth exhale puff, the pressure moves from the point 117 along a curve portion 118 towards the average line 111. After a brief initial time $t_1$, the curve portion 118 is within a tolerance range of, for example, 0.3 volts of the reference line 111 as represented by the dashed line 119.

According to another aspect of the invention, exhale mouth puffing is detected by determining when normal inspiration takes place and the expiration curve portion 118 is substantially flat or between the reference line 111 and the dashed line 119. Normal inspiration is assumed to take place if the inspiration portion 114 of the curve 113 exceeds a reference level, such as 0.5 volts above the reference line 111. A short time delay is allowed to elapse after expiration begins before looking at the level of the expiration curve in order to ignore any short duration peak 117. If, after this time delay, the expiration curve portion 118 is within 0.3 volts of the average level 111 and the previous inspiration curve level was at least 0.5 volts above the reference level 111, exhale mouth puffing is scored. It is necessary to look at both the inspiration portion and the expiration portion of the curve 113 to detect the occurrence of exhale mouth puffing. Looking at the inspiration portion of the curve 113 prevents possible confusion in distinguishing between exhale mouth puffing and apnea. As with mask leaks and open mouth breathing, the microcomputer is programmed to maintain the existing pressure in response to exhale mouth puffing. The pressure is increased only in response to the sensing of one or more respiratory events such as apnea events and is decreased only in response to either the absence of apnea for a predetermined time or an event which returns the apparatus 10 to the low pressure standby operating mode.

Snoring Signal Generation

Many clinicians want to know when and how often a patient snores, since it is an indicator of a potentially unstable airway. In the past, snoring was often detected by a microphone placed in the CPAP mask. This method of measuring snoring may be inaccurate since the CPAP mask can muffle the snoring sounds. A technician in a sleep clinic would manually note when a patient is snoring. In order to provide an accurate history of sleep events occurring while a patient sleeps, a recorder may be connected to the controller 17 (FIG. 1). The recorder may replace the sleep timer and record all important sleep events, including the total time the patient is wearing the mask 11, snoring, apnea events, mouth breathing, etc. The use of a recorder prevents inaccuracies, for example, when signals are weak or distorted, or when the technician is preoccupied with other duties.

According to a further aspect of the invention, the need for a microphone or any other extra device connected to the mask to detect snoring is eliminated. The propagation of sound in air, or in any medium for that matter, is generally thought of as localized alternating compression and rarefaction of that medium and is usually detected as such. Consequent to such localized pressure cycling within the medium there is of course localized mass flow cycling. The mass flow transducer in the preferred embodiment of the air flow sensor 15 is sufficiently sensitive to respond to the localized air flow variations caused by snoring and other sound at the CPAP mask 11 connected to the remote end of the tube 14.

Various authorities have taught that the audio frequency of snoring is within a range of from as low as 20 Hz. to as high as 150 Hz. In tests conducted by the inventors herein, it was found that for a range of patients, snoring has the highest signal to other noise ratio at about 70 Hz. However, it should be noted that snoring is not defined to occur exactly at 70 Hz., since snoring is not a pure tone. Snoring, like most other sounds, is comprised of a spectrum of frequencies. Since the signal-to-noise ratio obviously depends on noise as well as the snoring signal, the center frequency is determined in part by whatever noise rides on the flow signal and is inherent to the particular apparatus 10.

Figure 8:
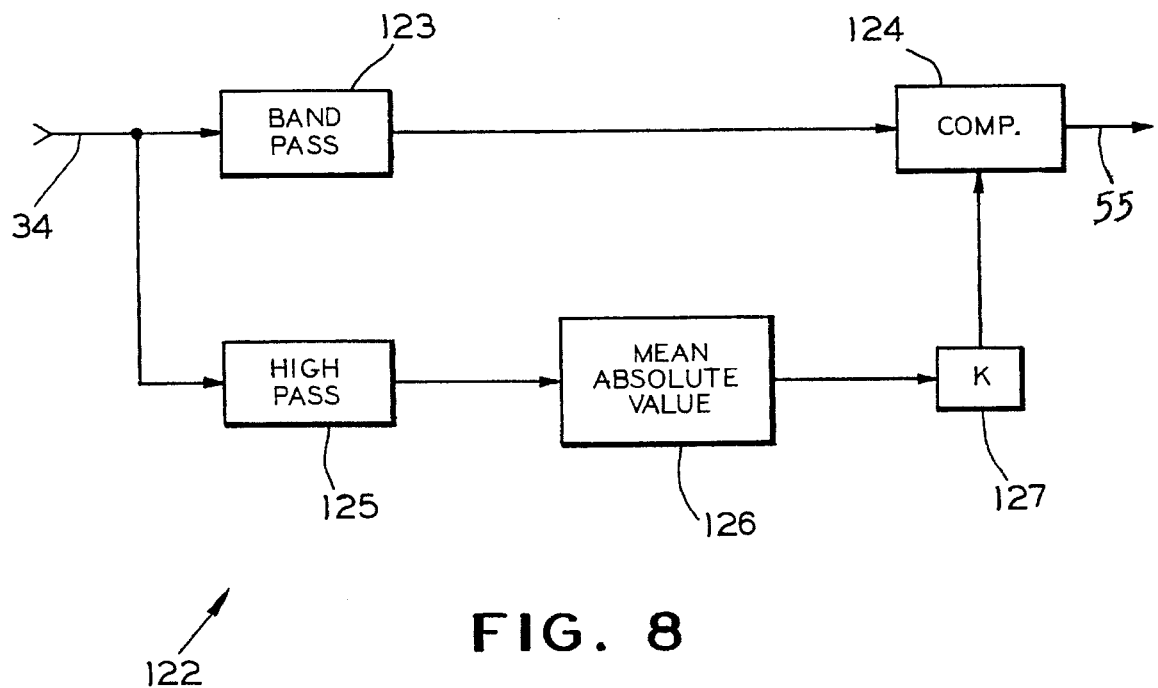
FIG. 8 is a schematic block diagram illustrating circuitry for detecting snoring according to the invention.

Referring now to FIG. 8, details are shown for the band pass filter and comparator 122. The gross flow signal on the input 34 (FIG. 2) is applied through a band pass filter 123 to one input of a comparator 124. It was discovered that the largest signal-to-noise ratio is attained when the center frequency of the filter 123 is centered at or around 70 Hz. and the passband is about 7 Hz. wide. Preferably, the filter 123 provides a signal gain within the passband and an increasing amount of attenuation as the noise frequency falls further outside of the passband. If, for example, the patient breaths into the mask 11 at a rate of 15 BPM or at a frequency of 0.25 Hz., there will be a substantial attenuation of noise relating to the gross air flow. There also will be an attenuation of any noise resulting from the spin frequency of the bearing balls for the blower 12 which, for example, may be on the order of 400 Hz. On the other hand, the filter 123 may be designed to provide a gain of about 20 or more for signals falling within the passband.

The output from the filter 123 will consist of any background noise falling within the passband frequency plus any snoring noise falling within the passband frequency. In order not to confuse the background noise with snoring, a threshold limit on the output of the band pass filter 123 is established that is high enough to minimize false positive snoring indications, but is low enough to minimize false negative snoring indications. The snoring threshold detection limit is established by passing the gross flow signal from the input 34 (FIG. 2) through a high pass filter 125, a mean absolute value circuit 126 and an amplifier 127 to the other input to the comparator 124. Preferably, the high pass filter 125 is a vcvs, 4th order Butterworth filter with a cutoff frequency of approximately 500 Hz. and a roll off of about 80 dB/decade. The filter 125 essentially eliminates any part of the signal caused by gross air movement and the sound of snoring. The filter 125 does pass a major portion of the signal due to noise other than snoring. The circuit 126 then produces a signal equal to the mean absolute value of the output of the high pass filter 125. The mean absolute value signal, with proper bias and gain from the amplifier 126, becomes the snoring threshold detection limit. In summary, the noise in the flow signal is used to generate the snoring threshold detection limit. As the flow signal becomes noisier as the CPAP pressure is adjusted upward, so does the out put of the band pass filter 123. If the snoring threshold limit were fixed, either more false positive indications of snoring would occur at higher pressures or more actual snoring events would be missed at lower CPAP pressures, depending on the level at which the threshold limit was set. But because the detection limit is determined by the level of noise in the flow signal, the incidents of false positive and false negative snoring indications are minimized at any noise level.

The output of the comparator 124 will be a logic signal having, for example, a low level in the absence of snoring and a high level whenever snoring occurs within the passband frequency of the filter 123. During snoring, the output of the comparator 124 will be a series of pulses, with a pulse produced each time the snoring threshold detection limit is crossed by the output of the bandpass filter 123. The output of the comparator 124 is applied to the microprocessor which counts the pulses during each breach cycle. If during a breathing cycle this number equals or exceed a predetermined number, such as 15, then at the end of that breath cycle the microprocessor generates and delivers to the recorder a square wave to show that snoring was detected at a particular time. The microprocessor may use this same output to the recorder for indicating other respiratory events. For example, two closely spaced pulsed may be delivered to the recorder whenever an apnea event is detected, three closely spaced pulses may be delivered to the recorder whenever exhale puffing is detected, and a continuous high logic level signal may be delivered to the recorder so long as high level air leaks such as open mouth breathing or significant mask leaks are detected. The recorder may be of various forms. The recorder may have a digital memory for recording respiratory events over a period of time in a form suitable for transferring the information to a digital computer for subsequent analysis. Or, the recorder may be of the graph type in which a paper record is gradually moved past a pen which is controlled by the microprocessor to record the time and occurrence of respiratory events and the type of event detected.

It will be appreciated that the scope of the claimed invention is broader than the above described preferred embodiment of the invention. For example, it will be appreciated that many of the control functions may be achieved either digitally with a programmable microprocessor or through electric analog circuitry. Various other modifications and changes may be made to the above described preferred embodiment of CPAP apparatus without departing from the spirit and the scope of the following claims.

We claim:

1. An improved method for controlling CPAP apparatus adapted to apply a positive airway pressure to a patient, said apparatus including an air blower and means for applying a positive air pressure from said blower through a hose to a mask adapted to be secured to a patient in communications through the patient's nose with the patient's respiratory airway, said apparatus including means for detecting abnormal breathing events and for automatically increasing the positive airway pressure applied to the patient in response to the detection of at least one abnormal breathing event, said method comprising the steps of:

a) detecting air leakage through the patient's mouth caused by the patient maintaining an open mouth while breathing blower air through the nose; and b) preventing an automatic pressure increase as a consequence of a predetermined high air leakage through the patient's open mouth.

2. A method for controlling CPAP apparatus, as set forth in claim 1, and further including the step of preventing an automatic pressure increase as a consequence of a predetermined high leakage between the mask and the patient.

3. A method for controlling CPAP apparatus, as set forth in claim 2, wherein said air leakage through the patient's mouth is detected by generating a signal representing the total air flow to the mask, passing the total air flow signal through a high pass filter to establish a signal representing the air flow to the patient's respiratory system and wherein the difference between said total air flow signal and said patient air flow signal represents the total of all leakages of air delivered through the hose including leakage through the patient's mouth, and wherein said automatic pressure increases are made only in response to a detection of at least one abnormal breathing event in the patient air flow signal.

4. A method for controlling CPAP apparatus, as set forth in claim 3, and further including the step of inhibiting automatic changes in the CPAP pressure when the total of all air leakages full within a predetermined range.

5. An improved method for controlling CPAP apparatus adapted to apply a positive airway pressure to a patient, said apparatus including an air blower and means for applying a positive air pressure from said blower through a hose to a mask adapted to be secured to a patient in communications through the patient's nose with the patient's respiratory airway, said apparatus including means for detecting abnormal breathing events and for automatically increasing the positive airway pressure applied to the patient in response to the detection of at least one abnormal breathing event, said method comprising the steps of:

a) detecting when the patient inhales air delivered through the mask to the patient's nose and in the same breath cycle exhales through the mouth; and b) preventing an automatic increase in the pressure applied to the patient's airway when nose inhalation and mouth exhalation are detected in the same breath cycle.

6. A method for controlling CPAP apparatus, as set forth in claim 5, wherein mouth exhalation is detected by detecting when both the inspiration air flow at the mask during a breath cycle exceeds a predetermined threshold level and at least a portion of the expiration air flow at the mask during such breath cycle is less than a predetermined threshold level.

7. A method for controlling CPAP apparatus, as set forth in claim 6, and further including the step of adjusting the predetermined threshold level upwardly in response to an increase in the patient air flow and downwardly in response to a decrease in the patient air flow.

8. A method for generating a square wave breathing signal indicative of patient inspiration and expiration into a mask comprising the steps of:

a) generating a patient air flow signal indicative of the air flow between the mask and the patient's respiratory system, the patient air flow signal having a predetermined level when there is no air flow between the mask and the patient's respiratory system;

b) generating an inspiration threshold signal having a level displaced from the predetermined level;

c) generating an expiration threshold signal separate from said inspiration threshold signal and having a level displaced from the predetermined level;

d) switching the breathing signal from a first logic level to a second logic level when the patient air flow signal crosses the inspiration threshold signal during inspiration;

and e) switching the breathing signal from said second logic level to said first logic level when the patient air flow signal crosses the expiration threshold signal during expiration.

9. A method for generating a square wave breathing signal indicative of patient inspiration and expiration into a mask comprising the steps of:

a) generating a patient air flow signal indicative of the airflow between the mask and the patient's respiratory system, the patient air flow signal having a predetermined level when there is no air flow between the mask and the patient's respiratory system;

b) generating an inspiration threshold signal having a level displaced from the predetermined level which is a function of the maximum difference between the patient air flow signal during inspiration and the predetermined level, wherein said inspiration threshold signal is generated by rapidly increasing differences between the inspiration threshold signal and the predetermined level in response to increases in the maximum difference between the patient air flow signal during inspiration and the predetermined level and by slowly decreasing differences between the inspiration threshold signal and the predetermined level in response to decreases in the maximum difference between the patient air flow signal during inspiration and the predetermined level;

c) generating an expiration threshold signal having a level displaced from the predetermined level which is a function of the maximum difference between the patient air flow during expiration signal and the predetermined level, wherein said expiration threshold signal is generated by rapidly increasing differences between the expiration threshold signal and the predetermined level in response to increases in the maximum difference between the patient air flow signal during expiration and the predetermined level and by slowly decreasing differences between the expiration threshold signal and the predetermined level in response to decreases in the maximum difference between the patient air flow signal during expiration and the predetermined level;

d) switching the breathing signal from a first logic level to a second logic level when the patient air flow signal crosses the inspiration threshold signal during inspiration;

and e) switching the breathing signal from said second logic level to said first logic level when the patient air flow 10. A method for generating a square wave breathing signal indicative of patient inspiration and expiration into the mask comprising the steps of:

a) generating a patient air flow signal indicative of the air flow between the mask and the patient's respiratory system, the patient air flow signal having a predetermined level when there is no air flow between the mask and the patient's respiratory system;

b) generating an inspiration threshold signal having a level displaced from the predetermined level which is a function of the maximum difference between the patient air flow signal during inspiration and the predetermined level;

c) generating an expiration threshold signal separate from said inspiration threshold signal and having a level displaced from the predetermined level which is a function of the maximum difference between the patient air flow during expiration signal and the predetermined level;

d) switching the breathing signal from a first logic level to a second logic level when the patient air flow signal crosses the inspiration threshold signal during inspiration;

e) switching the breathing signal from said second logic level to said first logic level when the patient air flow signal crosses the expiration threshold signal during expiration;

f) generating a total air flow signal indicative of the total air flow to the mask including any air lost due to leakage;

g) generating the derivative of the total air flow signal, said derivative having a second predetermined level when there is no air flow between the mask and the patient's respiratory system;

h) generating a first derivative threshold signal which is a function of the maximum difference between the total air flow derivative and the second predetermined level when the patient's breathing is changing from maximum expiration to maximum inspiration;

i) generating a second derivative threshold signal which is a function of the maximum difference between the total air flow derivative and the second predetermined level when the patient's breathing is changing from maximum inspiration to maximum expiration;

j) switching the breathing signal from the first logic level to the second logic level when the total air flow derivative exceeds the first derivative threshold signal while said patient air flow signal is between the inspiration and expiration threshold signal levels; and k) switching the breathing signal from the second logic level to the first logic level when the total air flow derivative exceeds the second derivative threshold signal while the patient air flow signal is between the inspiration and expiration threshold signal levels.

11. In CPAP apparatus adapted to apply a positive airway pressure to a patient, said apparatus including an air blower having a positive pressure output applied through a hose to a mask adapted to be secured to a patient in communications with the patient's respiratory airway, a method for detecting patient snoring comprising the steps of:

a) generating a signal corresponding to the mass air flow in the hose at the end of the hose which receives air from the blower;

b) passing said mass air flow signal through a band pass filter to obtain a first signal consisting primarily of snoring information and noise;

c) establishing a threshold signal based primarily on the level of non snoring noise in said mass air flow signal;

d) comparing said first signal to said threshold signal and generating a snoring signal whenever said first signal exceeds said threshold signal.

12. A method for detecting patient snoring in CPAP apparatus, as set forth in claim 11, and wherein said threshold signal is established by passing said mass air flow signal through a high pass filter which removes any low frequency noise and snoring noise to establish a second signal, generating the mean absolute value of said second signal and wherein said threshold signal is a function of the mean absolute value of said second signal.

13. A method for detecting patient snoring in CPAP apparatus, as set forth in claim 11, wherein said mass air flow signal is passed through a band pass filter having a center frequency of about 70 Hz and passband of about 7 Hz.

14. In CPAP apparatus which includes blower means for creating a positive air pressure, a mask adapted to be attached to a patient in communications with the patient's respirator system and a hose having a first end for receiving a flow of positive pressure air from said blower means and a second end for delivering such flow of positive pressure air to said mask, apparatus for detecting when a patient is snoring comprising means for generating a first electric signal indicative of the mass air flow at said first hose end, such mass air flow including a first component resulting from air flow from said blower means, a second component resulting from patient inspiration and expiration at said mask, a third component comprising noise resulting from patient snoring, and a fourth component comprising noise other than snoring noise, band pass filter means responsive to the first signal for establishing a second electric signal consisting of snoring and non snoring noise, means responsive to the fourth component of the first signal for establishing a snoring threshold level signal, and means for indicating the presence of snoring when the second signal exceed the snoring threshold level signal.

15. Apparatus for detecting when a patient is snoring, as set forth in claim 14, wherein said means responsive to the fourth component of the first signal for establishing a snoring threshold level signal comprises a high pass filter for removing the first, second and third components from the first signal to establish a third electric signal based on said forth component, and means responsive to the third signal for establishing the snoring threshold level signal as a function of the mean absolute value of the third signal.

* * * * *